(12) United States Patent
Branda et al.

(10) Patent No.: US 7,041,763 B2
(45) Date of Patent: May 9, 2006

(54) PHOTOCHROMIC POLYMERS AND METHODS OF SYNTHESIZING SAME

(75) Inventors: Neil R. Branda, North Vancouver (CA); Andrew J. Myles, Charlottetown (CA)

(73) Assignee: Simon Fraser University, Burnaby (CA)

( * ) Notice: Subject to any disclaimer, the term of this patent is extended or adjusted under 35 U.S.C. 154(b) by 265 days.

(21) Appl. No.: 10/332,944

(22) PCT Filed: Jul. 13, 2001

(86) PCT No.: PCT/CA01/01033

§ 371 (c)(1),
(2), (4) Date: Sep. 15, 2003

(87) PCT Pub. No.: WO02/06361

PCT Pub. Date: Jan. 24, 2002

(65) Prior Publication Data

US 2004/0030078 A1 Feb. 12, 2004

Related U.S. Application Data

(60) Provisional application No. 60/218,132, filed on Jul. 14, 2000.

(51) Int. Cl.
C08F 118/02 (2006.01)

(52) U.S. Cl. .................. 526/319; 526/346; 526/169; 526/171; 526/286

(58) Field of Classification Search ............... 526/319, 526/346, 169, 171, 286
See application file for complete search history.

(56) References Cited

U.S. PATENT DOCUMENTS 5,342,909 A * 8/1994 Grubbs et al. ............. 526/171
6,479,604 B1 * 11/2002 Kim et al. ................. 526/242

FOREIGN PATENT DOCUMENTS

| EP | 0 698 605 | * | 2/1996 |
| JP | 06-240242 | * | 8/1994 |
| JP | 11-256147 | * | 9/1999 |

OTHER PUBLICATIONS

Nakashima et al. "Synthesis of Polystyrene and Poly(alkyl methacrylate)s having Photochromic Dithienylethene Pendant Groups", Polymer Journal, 30(12), 985–989 (Dec. 1998).*

Kim et al. "Photoinduced Refractive Index change of a Photochromic Diarylethene Polymer" Macromolecules, 32(15) 4855–4860 (Jul. 1990).*

Irie et al. "Photochromism of Diarylethenes having Thiophene oligomers as the Aryl Groups", Tetrahedron, 53(36), 12263–12271 (Sep. 1997).*

* cited by examiner

Primary Examiner—Ling-Siu Choi
(74) Attorney, Agent, or Firm—Oyen Wiggs Green & Mutala

(57) ABSTRACT

Ring-opening metathesis polymerization (ROMP) of a photochromic 1,2-bis-(3-thienyl)-cyclopentene monomer generated a series of novel polymers. All polymers exhibit reversible light-activated interconversion between their colorless-open and their colored-closed forms.

-continued
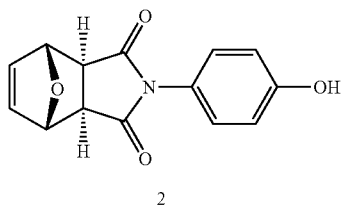
2
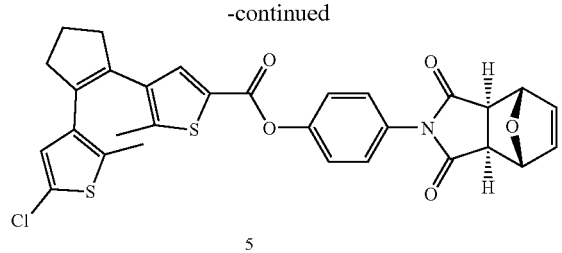
5
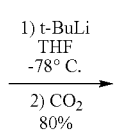
3
1) t-BuLi
   THF
   -78° C.
2) CO₂
   80%
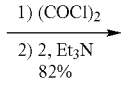
4
1) (COCl)₂
2) 2, Et₃N
   82%
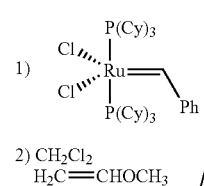
1) 
2) CH₂Cl₂
   H₂C=CHOCH₃
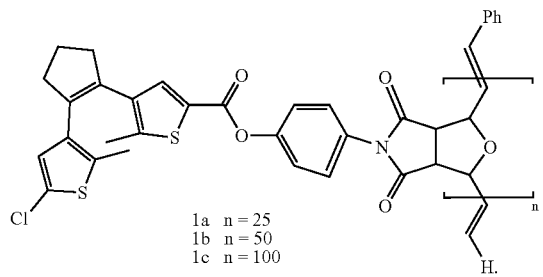
1a  n = 25
1b  n = 50
1c  n = 100
44 Claims, 5 Drawing Sheets

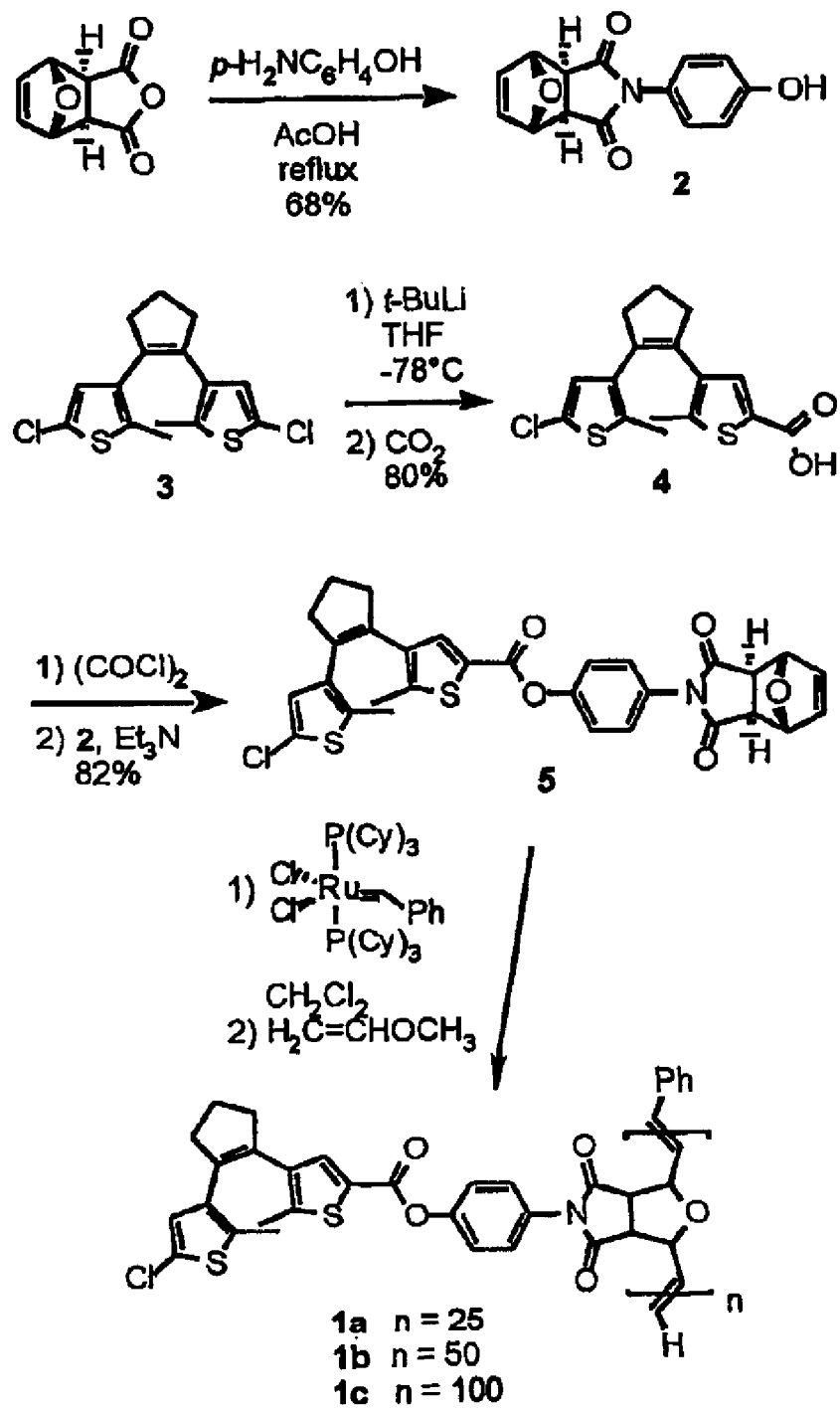
Figure 1 – Preparation of Homopolymers 1a-1c

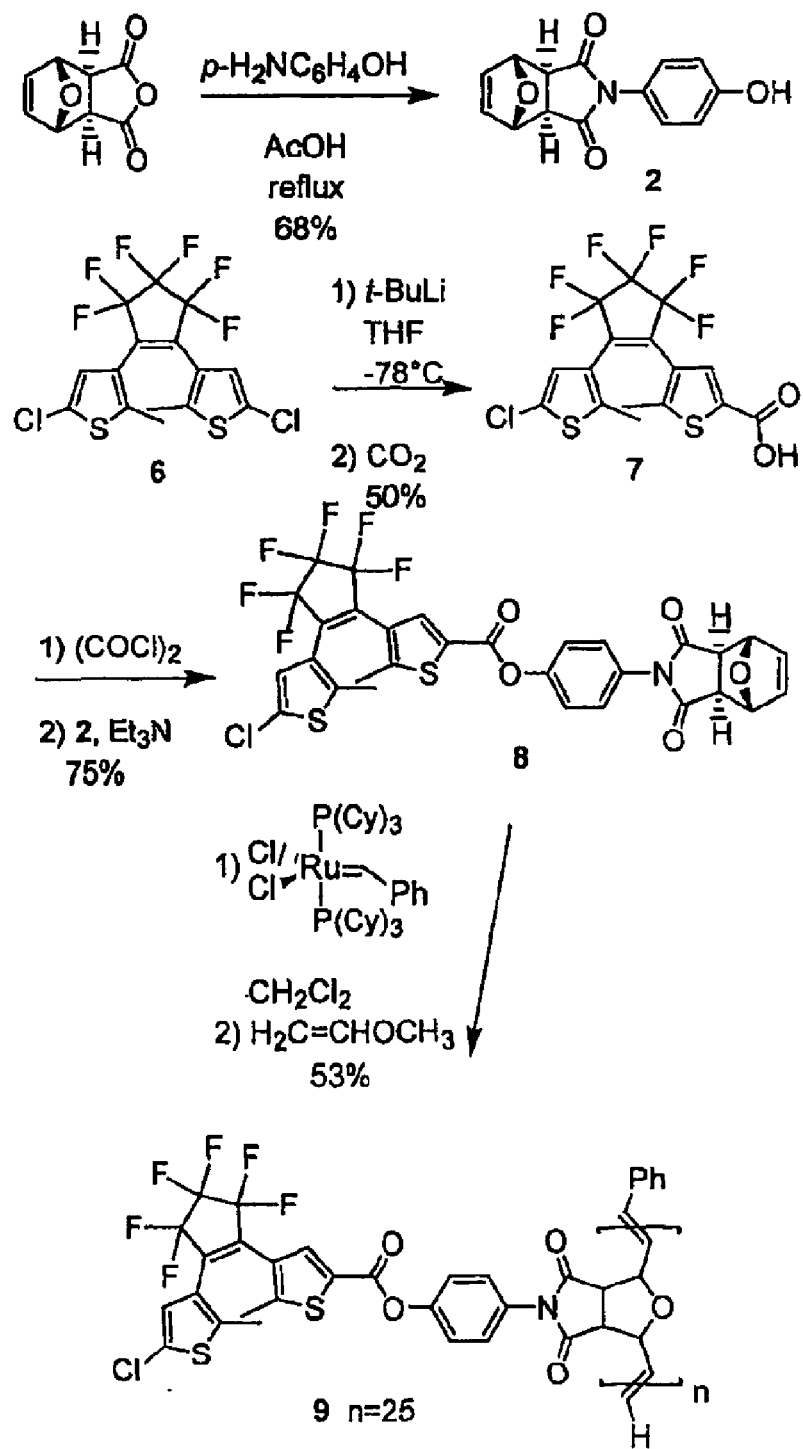
Figure 3 – Preparation of Flourinated Homopolymer 9

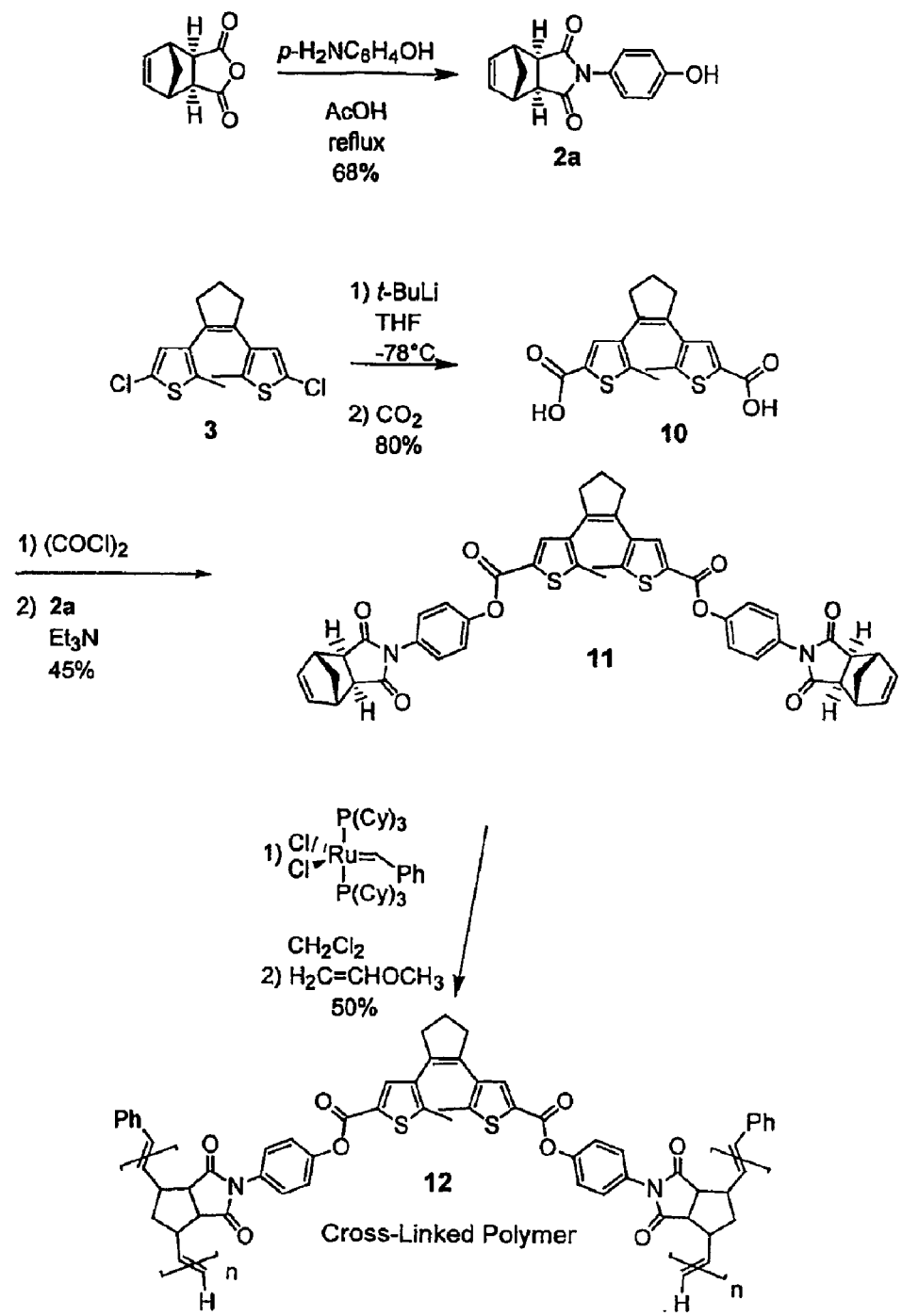
Figure 4 – Preparation of Cross-linked Homopolymer 12

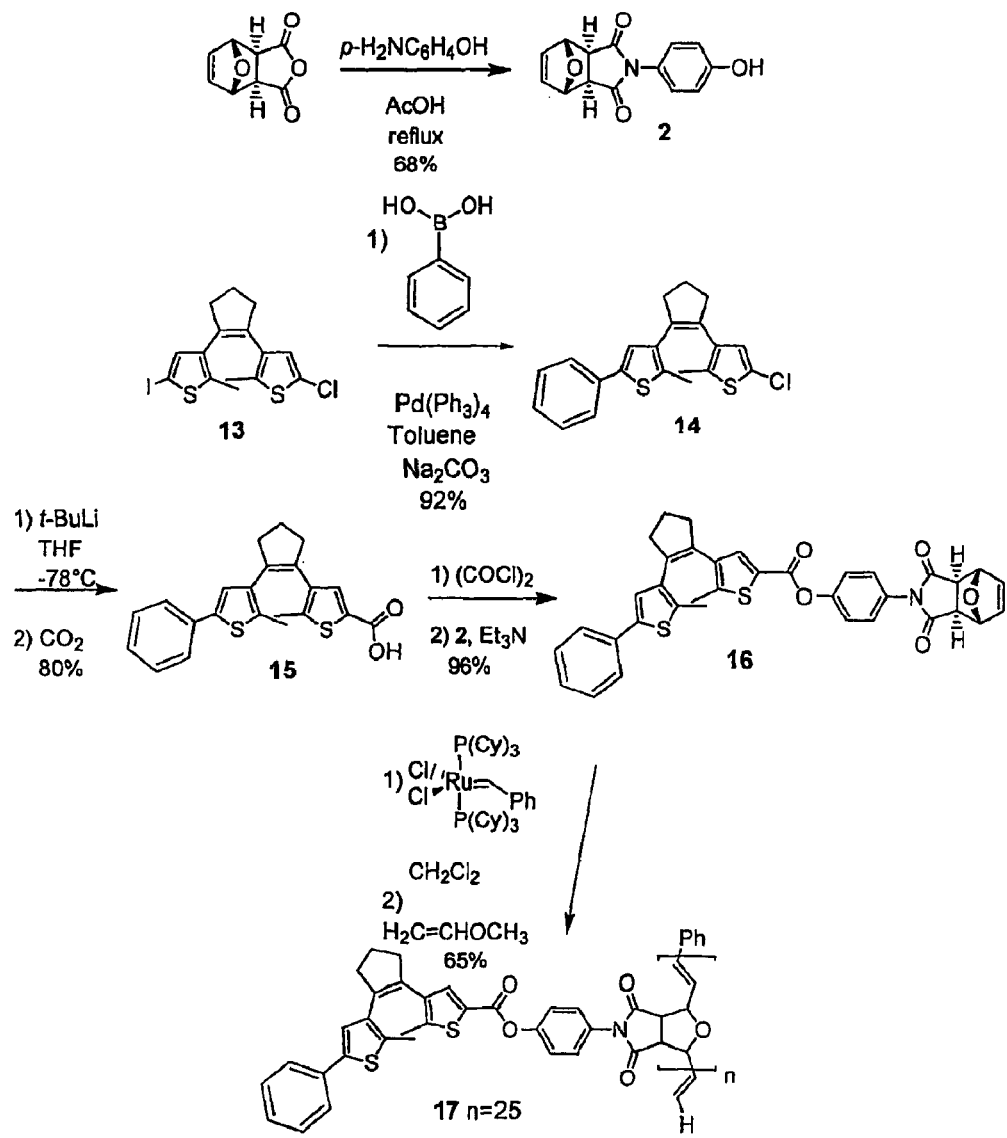
Figure 5 – Preparation of Phenyl Homopolymer 17

PHOTOCHROMIC POLYMERS AND METHODS OF SYNTHESIZING SAME

REFERENCE TO RELATED APPLICATIONS

This application is the United States national stage of International Application No. PCT/CA01/01033, filed Jul. 13, 2001, and claims the benefit of U.S. Provisional Patent Application No. 60/218,132, filed Jul. 14, 2000.

FIELD OF THE INVENTION

The present invention relates to novel photochromic polymers, methods of preparing the photochromic polymers and all uses of the novel photochromes for example in optical materials and photonic devices.

BACKGROUND OF THE INVENTION

The photochromism of 1,2-bis-(3-thienyl)-cyclopentene derivatives involves the reversible photoinduced cyclization between the colorless-open and the colored-closed forms of the chromophore[1]. This phenomenon is interesting for its potential role in optical materials and photonic devices such as variable-transmission filters, optical information storage systems and photo-regulated molecular switches[2]. The need for practical handling of definite forms of photochromic materials such as films, sheets, fibers or beads, dictate the use of polymeric rather than monomeric photochromes[3,4]. Homopolymers (i.e. polymers derived from one species of monomer) are more desirable than copolymers as they will have an increased density of the photochromic unit within the material. This translates into a greater amount of information expressed or stored per unit volume or surface.

Existing polymerization processes rely on harsh reaction conditions which limits the structure of photochromic products. The present invention employs very mild reaction conditions which allows compatibility and flexibility, including the capacity to synthesize products having a variety of pendant functional groups. The chemistry can be controlled and therefore macroscopic properties may be tailored.

In view of the foregoing, there is a need in the art to develop novel photochromic homopolymers and methods of synthesizing same.

SUMMARY OF THE INVENTION

The present invention relates to novel homopolymers of the Formula I:

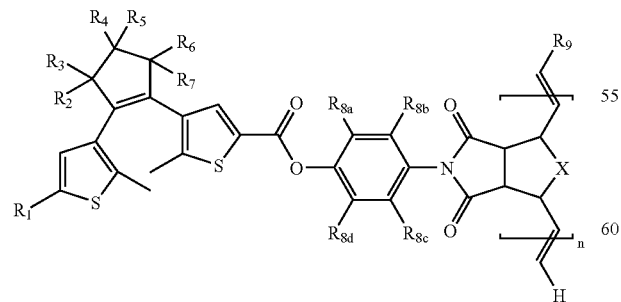

(I)

wherein n is any integer; X is $CH_2$, $CHR_{10}$, O, S, NH, N-alkyl, N-aryl or $CH_2$—$CH_2$; $R_1$ is selected from the group consisting of H, a halogen, a carboxylic acid, an ester, an aldehyde, an alkene, a phenyl, an aryl and structure A where structure A is:

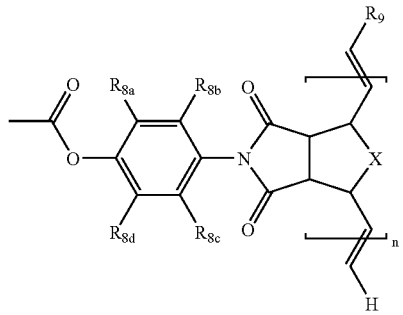

$R_2$, $R_3$, $R_4$, $R_5$, $R_6$ and $R_7$ are each selected from the group consisting of H and a halogen; $R_{8a}$, $R_{8b}$, $R_{8c}$ and $R_{8d}$ are each selected from the group consisting of H, an alkyl and a halogen; $R_9$ is a phenyl or an aryl; and $R_{10}$ is an alkyl, an aryl or a phenyl. Preferably, n is from about 16 to about 100, $R_1$ is chlorine, phenyl or structure A, $R_2$–$R_7$ is H or F, $R_{8a}$–$R_{8d}$ is H, $R_9$ is phenyl and X is O or $CH_2$.

The novel photochromic homopolymers of the invention are prepared using ring-opening metathesis polymerization (ROMP) of a photochromic 1,2-bis-(3-thienyl)-cyclopentene monomer. All novel polymers of the invention exhibit reversible light-activated interconversion between their colorless-open and their colored-closed forms.

BRIEF DESCRIPTION OF THE DRAWINGS

FIG. 1 is a schematic drawing showing the preparation of photochromic homopolymer 1 of the invention.

FIG. 3 is a schematic drawing showing the preparation of photochromic homopolymer 9 of the invention.

FIG. 4 is a schematic drawing showing the preparation of photochromic homopolymer 12 of the invention.

FIG. 5 is a schematic drawing showing the preparation of photochromic homopolymer 17 of the invention.

DETAILED DESCRIPTION OF THE INVENTION

Figure 2:
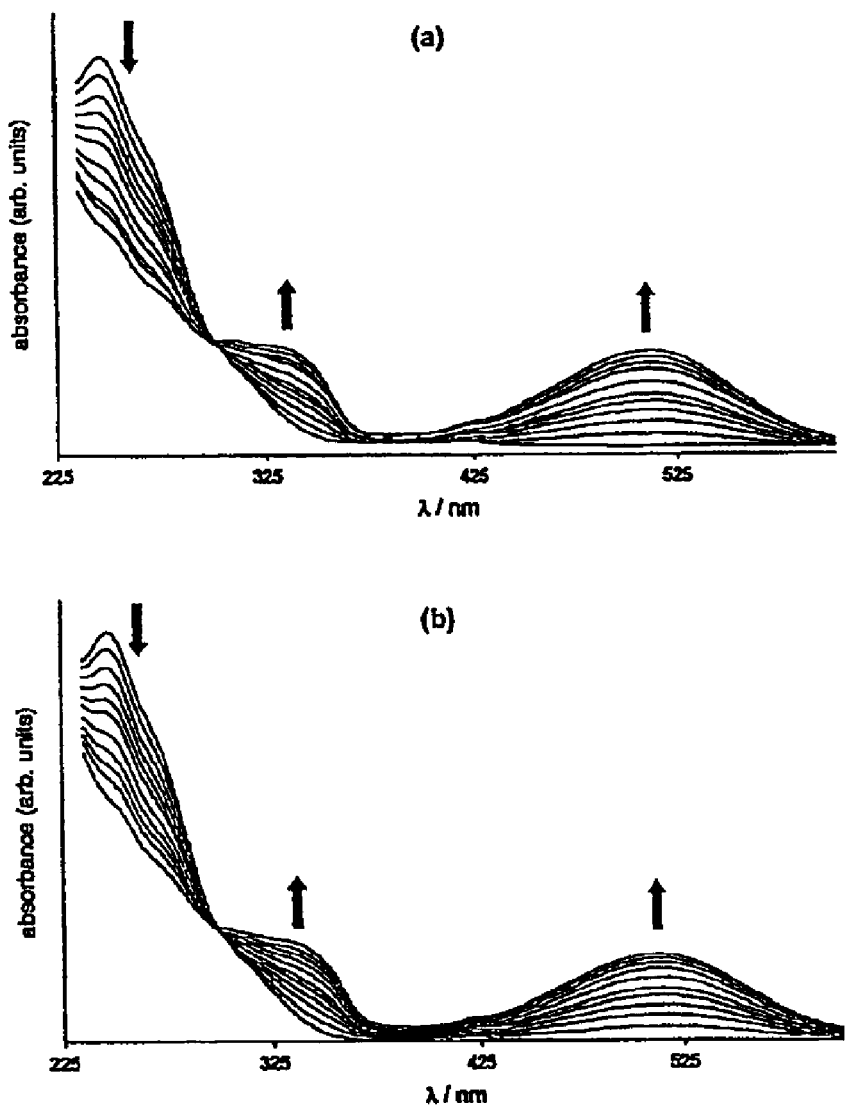
FIGS. 2(a) and 2(b) are graphs showing changes in the UV-Vis absorption spectra of THF solutions of (a) monomer 5 ($3 \times 10^{-5}$ M) and (b) polymer 1a ($3 \times 10^{-5}$ M with respect to the 1,2-bis-(3-thienyl)-cyclopentene photochrome) upon irradiation with 254 nm light. Irradiation periods are 2, 4, 6, 8, 10, 15, 20, 25, 30 and 40 seconds.

As hereinbefore mentioned, the present invention relates to novel photochromic homopolymers of the Formula I:

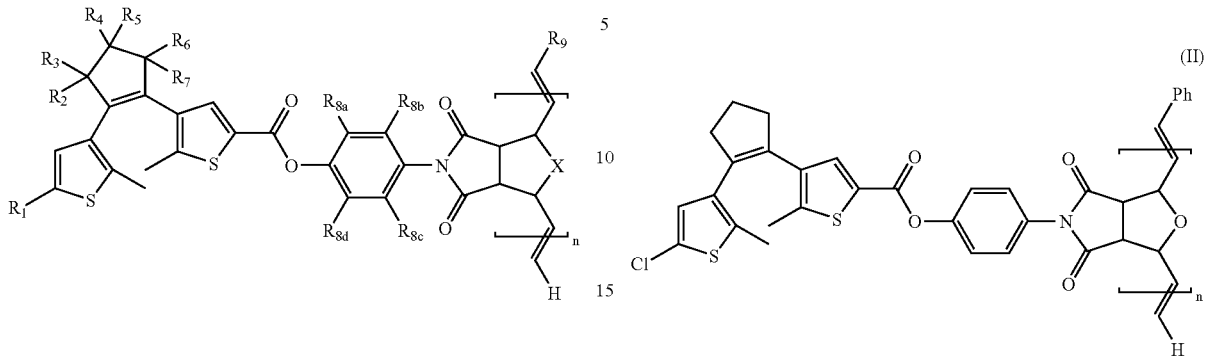

(I)

wherein n is any integer, X is $CH_2$, $CHR_{10}$, O, S, NH, N-alkyl, N-aryl or $CH_2$—$CH_2$; $R_1$ is selected from the group consisting of H, a halogen, a carboxylic acid, an ester, an aldehyde, an alkene, a phenyl, an aryl and structure A where structure A is:

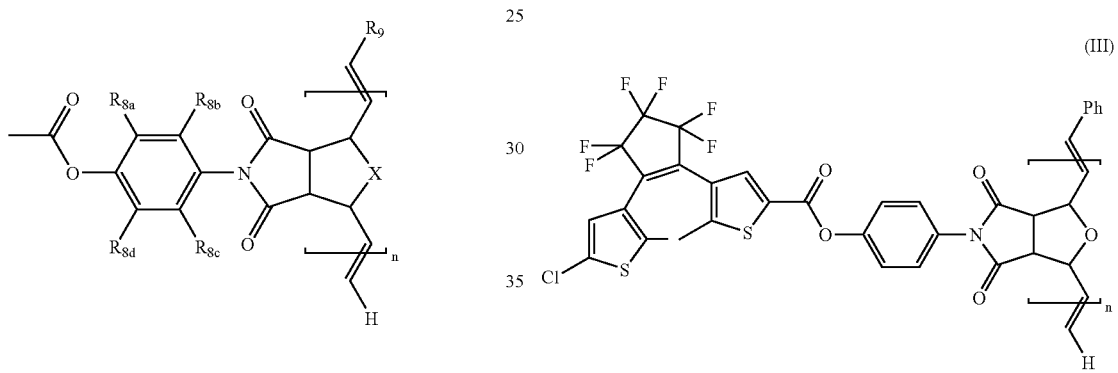

$R_2$, $R_3$, $R_4$, $R_5$, $R_6$ and $R_7$ are each selected from the group consisting of H and a halogen; $R_{8a}$, $R_{8b}$, $R_{8c}$ and $R_{8d}$ are each selected from the group consisting of H, an alkyl and a halogen; $R_9$ is a phenyl or an aryl; and $R_{10}$ is an alkyl, an aryl or a phenyl.

Preferably, the homopolymer is of the Formula II (II)

wherein n is from about 10 to about 100.

Other preferred homopolymers of the present invention include the flourinated homopolymer of Formula III, (III)

the cross-linked homopolymer of Formula IV, (IV)

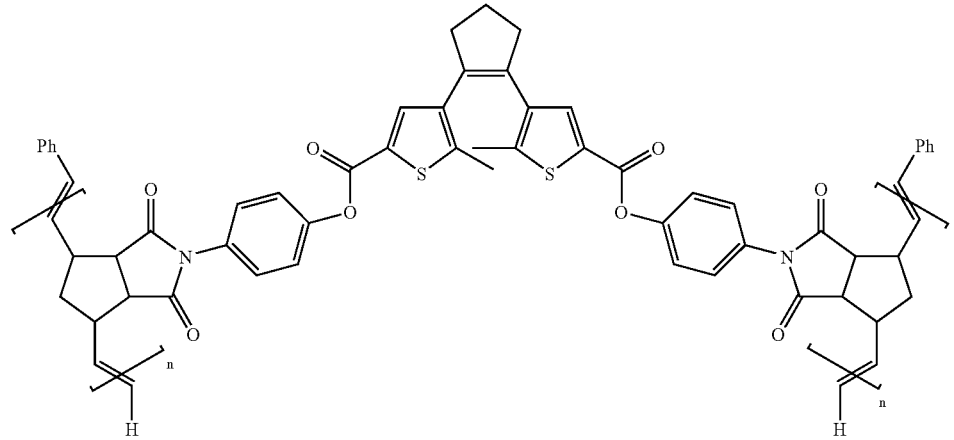

and the phenyl homopolymer of Formula V

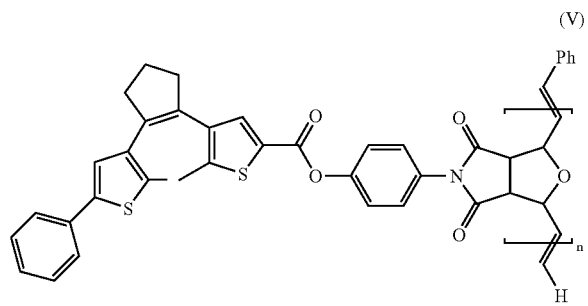

(V)

wherein n is from about 10 to about 100 for each of Formulas III, IV and V.

The homopolymers of the invention are prepared by ring-opening metathesis polymerization (ROMP) of a photochromic 1,2-bis-(3-thienyl)-cyclopentene monomer. The preparation of homopolymers of the Formulas II, III, IV and V are described in detail in Examples 1, 2, 3 and 4 below and are shown in FIGS. 1, 3, 4 and 5, respectively. The ROMP process is also described in U.S. Pat. No. 5,849,851 which is incorporated herein by reference.

Photochromes based on 1,2-bis-(3-thienyl)-cyclopentene derivatives offer many advantages. For example 1,2-bis-(3-thienyl)-cyclopentene derivatives possess optimal photochromic properties, including thermal irreversibility and fatigue resistance. In addition, the wavelength of light expressed in the colored forms can be readily tuned by tailoring the electronic distribution in the conjugated pathway created upon cyclization. This is most conveniently accomplished by modifying pendant functional groups (R) located on the heterocycles as shown below in the reaction scheme that illustrates the photoinduced interconversion between the colorless-open and colored-closed form of the 1,2-bis-(3-thienyl)-cyclopentene photochrome.

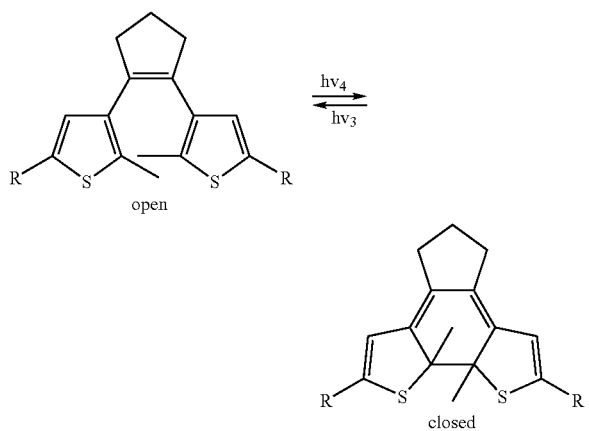

The inventors determined that in order to take full advantage of all possible pendant groups so that a wider range of colors can be expressed by the polymers, a mild and tolerant reaction polymerization protocol must be found. The inventors further determined that ring-opening metathesis polymerization (ROMP) techniques[5] provide the desired conditions and thus do not limit the pool of pendant R groups that can be used. As a result, the R group can be any functional group including, but not limited to, a halogen, a carboxylic acid, an ester, an aldehyde, an alkene or structure A.

Advantageously, the ROMP process produces homopolymers rather than copolymers. This provides macroscopic materials that have an increased density of photochromic units, a feature that is very advantageous for practical applications. Another advantage of using the ROMP technology is that by varying the catalyst-to-substrate stoichiometry, ROMP allows the polymer chain length to be readily and precisely tailored.

The present application represents the first example of photochromic homopolymers synthesized using ROMP technology[6]. The result is an unprecedented series of well-ordered homogeneous homopolymers that reversibly undergo changes in color when irradiated with light of appropriate wavelength. Color changes are, for example, colorless-to-red or colorless-to-purple. These colors can be easily tuned by simple tailoring of the photochrome's pendant groups.

The present invention includes all uses of the novel homopolymers of the inventions. These uses include, but are not limited to, (1) opthalmic lenses-eyeglasses that change color depending on the ambient light;
(2) actinometry, and molecular sensors;
(3) novelty items such as photochromic inks, paints and fibers;
(4) variable transmission filters—those that on command, regulate the amount and type of light that can be transmitted;
(5) high-density optical information storage systems (this invention is particularly well-suited to this application as it provides more information storage sites per unit area);
(6) photo-regulated molecular switches that can be incorporated into molecular-scale machinery;
(7) optoelectronic systems; and
(8) reversible holographic systems.

As will be appreciated by a person skilled in the art, co-polymers or other polymers comprising the photochromic units of the present invention may also readily be produced utilizing ROMP technology. Such other polymers are within the scope of the present invention.

In other embodiments of the invention, the polymerization protocol described herein, including ROMP techniques and the use of Grubbs' catalyst, may be used in connection with other photochromic monomers, including an anhydride variant to derive the anhydride polymer shown below:

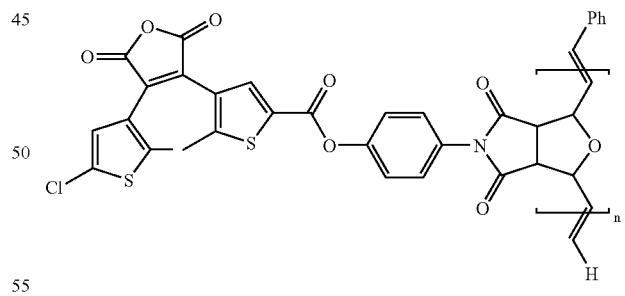

EXAMPLES

The following examples will further illustrate the invention in greater detail although it will be appreciated that the invention is not limited to the specific examples.

Experimental Methods

Tetrahydrofuran (THF) (Caledon) was distilled over sodium/benzophenone ketyl radical under argon. $CH_2Cl_2$ (Caledon) was distilled over calcium hydride under argon. All other solvents were used as received. Solvents for NMR analysis (Cambridge Isotope Laboratories) were used as received. Bis(tricyclohexylphosphine)benzylidine ruthenium(IV)dichloride (Grubbs' catalyst)[7] was purchased from Strem and was stored and weighed in a glove box under a nitrogen atmosphere. All other reagents and starting materials were purchased from Aldrich. Compounds 7-oxa-bicyclo[2.2.1]hept-5-ene-2,3-dicarboxylic anhydride[8], 2a[9], 3[10], 6[11], and 10[12] were prepared as described in the literature and as would be readily apparent to a person skilled in the art. Compound 13 was prepared in a fashion analogous to the synthesis of compound 4 except that carbon dioxide was replaced with iodine as would be readily apparent to a person skilled in the art.

All polymerization reactions were carried out on a Schlenk line. Gel permeation chromatography (GPC) analyses (calibrated by polystyrene) were performed on THF solutions of the polymers using a Waters 515 HPLC pump and 2410 Refractive Index Detector at a flow rate of 1.0 mL/minute through a 7.8×300 mm column at 30° C. $^1$H NMR characterizations were performed on a Varian Inova-300 instrument, working at 299.96 MHz. Chemical shifts ($\delta$) are reported in parts per million relative to tetramethylsilane using the residual solvent peak as a reference standard. Coupling constants (J) are reported in Hertz. FT-IR measurements were performed using a Nicolet Magna-IR 750. UV-Vis measurements were performed using a Pharmacia Biotech Ultraspec 3000 spectrophotometer.

Preparation of Homopolymers

Example 1

Preparation of Homopolymer 1 (FIG. 1)

Step 1—Synthesis of Olefin Fragment 2

A mixture of 7-oxa-bicyclo[2.2.1]hept-5-ene-2,3-dicarboxylic anhydride (2.0 g, 12 mmol) and p-aminophenol (1.31 g, 12 mmol) were heated at reflux for 10 minutes in glacial acetic acid (3 mL), after which time a precipitate formed. The reaction mixture was cooled to room temperature and the product was collected by filtration, washed with water and dried in vacuo to afford 2.1 g (68%) of the olefin fragment exo-N-(p-hydroxyphenyl)-3,6-epoxy-4-cyclohexene-1,2-dicarboximide 2 as a white solid: $^1$H NMR (DMSO-$d_6$) $\delta$ 9.71 (s, 1H), 6.95 (d, J=8.75 Hz, 2H), 6.83 (d, J=8.75 Hz, 2H), 6.58 (s, 2H), 5.21 (s, 2H), 3.02 (s, 2H); $^{13}$C NMR (DMSO-$d_6$) $\delta$ 175.95, 157.27, 136.53, 127.98, 123.19, 115.38, 80.66, 47.20; EIMS (m/z): 257 (M$^+$), 189 (M$^+$–C$_4$H$_4$O); FTIR $\bar{v}$ 3334 (s, broad), 3143, 3102, 3076, 3049, 3029, 2973, 1697, 1612, 1594.

Step 2—Synthesis of Carboxylic Acid 4

A solution of dichloride 3 (385 mg, 1.17 mmol) in dry THF (50 mL) at −78° C. under argon was treated with tert-butyllithium (0.7 mL of 1.7 M solution in hexane, 1.17 mmol). After stirring for 15 minutes, excess dry CO$_2$ was bubbled through the solution. The reaction mixture was warmed to room temperature, quenched with dilute HCl, extracted with Et$_2$O (3×50 mL), dried over Na$_2$SO$_4$ and evaporated in vacuo. Purification by column chromatography through silica (5% CH$_3$OH—CH$_2$Cl$_2$) afforded 318 mg (80%) of the product 4 as a pale yellow solid: $^1$H NMR (CDCl$_3$) $\delta$ 7.55 (s, 1H), 6.52 (s, 1H), 2.72 (m, 4H), 1.99 (m, 5H), 1.80 (s, 3H).

The yield of the monoanion in the lithiation step is greater than would be expected from a statistically governed product distribution. This may be attributed to the unfavorable charge build-up that would exist if both chlorine atoms underwent metal-halogen exchange reactions. This charge build-up is still significant despite the fact that the two thiophene rings are cross-conjugated instead of directly conjugated, suggesting the charge-charge repulsion between two thiophene heterocycles would be felt through space.

Step 3—Synthesis of Monomer 5

A vigorously stirred solution of carboxylic acid 4 (136 mg, 0.4 mmol) and 5 drops of DMF in CH$_2$Cl$_2$ (4 mL) at 0° C. was treated with a solution of oxalyl chloride (254 mg, 2.0 mmol) in CH$_2$Cl$_2$ (6 mL) dropwise over 10 minutes. After stirring at room temperature under argon for 2 hours, the reaction mixture was concentrated to dryness in vacuo. The residue was dissolved in CH$_2$Cl$_2$ (10 mL) and added dropwise over 10 minutes to a solution of olefin 2 (154 mg, 0.6 mmol) and triethylamine (0.5 mL) in acetone cooled to 0° C. The mixture was stirred overnight under argon and the solvent was removed in vacuo. Purification by column chromatography through silica (2% CH$_3$OH—CHCl$_3$) afforded 188 mg (82%) of the product as a pale yellow solid: $^1$H NMR (CDCl$_3$) $\delta$ 7.67 (s, 1H), 7.31 (m, 4H), 6.56 (s, 3H), 5.38 (m, 2H), 3.00 (s, 2H), 2.76 (m, 4H), 2.05 (m, 5H), 1.87 (s, 3H); $^{13}$C NMR (CDCl$_3$) $\delta$ 175.22, 159.95, 150.56, 144.60, 137.19, 136.78, 136.02, 135.33, 134.75, 134.14, 133.36, 129.16, 128.03, 127.62, 126.66, 125.59, 122.38, 81.51, 47.59, 38.61, 38.52, 22.89, 14.98, 14.30; ESMS(+ive): 600.0 (M+Na$^+$), 532 (M–Cl); IR (KBr-cast): 3050 (w), 2951 (w), 2843 (w), 1713 (s), 1202 (s).

Step 4—Polymerization of Bicyclic Olefin 5 to Yield Polymers 1(a)–(c)

ROMP reactions of monomer 5 were performed under rigorously inert conditions in a Schlenk tube. In a typical procedure a solution of monomer 5 in dry deoxygenated CH$_2$Cl$_2$ was canulated into a CH$_2$Cl$_2$ solution of bis (tricyclohexylphosphine)benzylidine ruthenium(IV) dichloride (Grubbs' catalyst) (0.04 equivalents for 1a, 0.02 equivalents for 1b, and 0.01 equivalents for 1c). The final monomer concentrations were 0.1 M. After stirring at room temperature for 14 hours, excess ethylvinyl ether was added and the solutions were stirred exposed to the atmosphere for 30 minutes. The polymers were precipitated in pure form by pouring the reaction solutions into cold Et$_2$O and collecting the precipitates by vacuum filtration (yields: 75% for 1a, 78% for 1b, and 75% for 1c). Homopolymers with varying molecular weights were synthesized in a systematic fashion by changing the molar amount (1–4 mol %) of Grubbs' catalyst used to initiate the reaction. In all cases, the ROMP reactions were reproducible, affording polymers 1a–c as off-white powders in good yields (~75%).

The success of the polymerization reactions was assessed by using $^1$H NMR spectroscopy. In the $^1$H NMR spectrum of monomer 5, the peak corresponding to the methine proton of the bicyclic olefin overlaps with the peak corresponding to the hydrogen on the chlorothiophene heterocycle at 6.56 ppm resulting in the area under the peak integrating to 3 protons. After the polymerization reactions, the peak at 6.56 ppm integrated to only 1 proton with respect to the other thiophene proton at 7.67 ppm. A new peak for the olefin protons appeared at 6.10 ppm. A typical $^1$H NMR (CDCl$_3$) is as follows: $\delta$ 7.6 (br s), 7.3 (br s), 6.6 (br s), 6.1 (br s), 5.8 (m), 5.2 (m), 4.6 (m), 3.4 (br s), 2.7 (br s), 2.0 (m), 1.8 (br s). The GPC characterization of the polymeric products is set forth in Table 1.

The polymeric products were all readily soluble in common organic solvents such as chloroform, dichloromethane, tetrahydrofuran and benzene. They are air-stable solids of reasonable number-average molecular weights (Mn) and relatively narrow polydispersities (Mw/Mn) as determined by gel permeation chromatographic analyses calibrated by polystyrene (Table 1).

Table 1 also summarizes the UV-Vis absorption properties of THF solutions of the novel polymers along with those for monomers 5, 8, 11 and 16. Polymers 1a–c, for example, show typical absorbances for the colorless-open forms of the 1,2-bis-(3-thienyl)-cyclopentene photochrome at 248 nm. Photo-induced isomerization studies were carried out by irradiating the THF solutions of 1a–c at 254 nm with a short-wavelength hand held lamp. Spectral changes were monitored in the UV-Vis region (FIG. 2). In all cases, irradiation produced an immediate decrease in the absorbances corresponding to the open form of the dithienylethene photochrome at 248 nm. The decrease in these absorbances was accompanied by the appearance of broad absorbances for the pink closed form of the photochrome centered at 512 nm. A typical irradiation time appropriate to effect quantitative ring closure is 40 seconds for solutions at $3 \times 10^{-5}$ M concentrations. The similarity of the absorption spectrum (values of $\lambda_{max}$ and $\epsilon$) for monomer 5 and those of the polymers in both open and closed forms illustrates that the intimacy of the photochromes covalently linked to the polymer backbone affects neither the ground-state nor the excited-state properties of the photochrome. As shown in Table 1, similar results were found in respect of the other homopolymers of this invention.

The polymers can be easily decolorized by subsequent irradiation for 1 minute with light of wavelength greater than 434 nm using a high power-lamp with an appropriate cutoff filter. The photoisomerization process is thermally irreversible, and solutions of the closed forms kept in the dark showed no changes in their absorption spectra.

The polymers were very robust, and their thin films were easily cast by layering toluene solutions of 1a–c onto water. After slow evaporation of the toluene, the resulting transparent films were transferred to slides.

Transmission electron microscopy of the films reveals a smooth surface possessing no topological features. These films immediately turned from colorless to pink when exposed for brief periods (60 seconds) at 254 nm. As with the polymers in solution, the films could be decolorized with above 434 nm light.

Example 2

Preparation of Flourinated
Homopolymer 9 (FIG. 3)

Step 1—Synthesis of Carboxylic Acid 7

A solution of dichloride 6 (500 mg, 1.14 mmol) in dry THF (50 mL) at –78° C. under argon was treated with tert-butyllithium (0.68 mL of 1.7 M solution in hexane, 1.14 mmol). After stirring for 15 minutes, excess dry $CO_2$ was bubbled through the solution. The reaction mixture was warmed to room temperature, quenched with dilute HCl, extracted with $Et_2O$ (3×50 mL), dried over $Na_2SO_4$ and evaporated in vacuo. Purification by column chromatography through silica (5% $CH_3OH$—$CH_2Cl_2$) afforded 260 mg (51%) of the product as a white solid: $^1H$ NMR ($CDCl_3$) $\delta$ 7.83 (s, 1H), 6.85 (s, 1H), 2.02 (s, 3H), 1.83 (s, 3H).

Step 2—Synthesis of Monomer 8

A vigorously stirred solution of carboxylic acid 7 (254 mg, 0.57 mmol) and 5 drops of DMF in $CH_2Cl_2$ (8 mL) at 0° C. was treated with a solution of oxalyl chloride (361 mg, 2.8 mmol) in $CH_2Cl_2$ (4 mL) dropwise over 10 minutes. After stirring at room temperature under argon for 2 hours, the reaction mixture was concentrated to dryness in vacuo. The residue was dissolved in $CH_2Cl_2$ (8 mL) and added dropwise over 10 minutes to a solution of olefin 2 (221 mg, 0.86 mmol) and triethylamine (0.5 mL) in acetone cooled to 0° C. The mixture was stirred overnight under argon and the solvent was removed in vacuo. Purification by column chromatography through silica ($CHCl_3$) afforded 75% yield of the product as a pale yellow solid: $^1H$ NMR ($CDCl_3$) $\delta$ 7.91 (s, 1H), 7.33 (m, 4H), 6.88 (s, 1H), 6.56 (m, 2H), 5.39 (m, 2H), 3.01 (s, 2H), 2.04 (s, 3H), 1.88 (s, 3H); $^{13}C$ NMR ($CDCl_3$) $\delta$ 175.20, 159.12, 150.19, 140.64, 136.79, 134.56, 130.66, 129.50, 128.40, 127.74, 126.02, 125.48, 123.91, 122.25, 81.52, 47.59, 15.08, 14.52.; ESMS(+ive): 703.1 ($M+NH_4^+$, 100%); IR (KBr-cast): 3015 (w), 1714 (s).

Step 3—Polymerization of Bicyclic Olefin 8 to Yield Polymer 9

The procedure is identical to that for the polymerization of olefin 5 except that the polymer was precipitated by adding MeOH instead of $Et_2O$. Thus 8 (37 mg, 0.056 mmol) was polymerized with Grubbs' catalyst (1.8 mg, 0.04 equivalents) to yield polymer 9 in 53% yield: $^1H$ NMR ($CDCl_3$) $\delta$ 7.9 (br s), 7.3 (br s), 6.9 (br s), 6.1 (br s), 5.8 (m), 5.2 (m), 4.6 (m), 3.4 (br s), 2.0 (m), 1.8 (br s). GPC: Mn=7437, Mw=10953, Polydispersity Index=1.47. Polymer 9 exhibited a color change from colorless to purple upon irradiation with 254-nm light.

Example 3

Preparation of Cross-linked
Homopolymer 12 (FIG. 4)

Step 1—Synthesis of Diolefin Monomer 11

A vigorously stirred solution of dicarboxylic acid 10 (375 mg, 1.08 mmol) and DMF (0.1 ml) in $CH_2Cl_2$ (20 mL) at 0° C. was treated with a solution of oxalyl chloride (2.02 g, 16 mmol) in $CH_2Cl_2$ (10 mL) dropwise over 10 minutes. After stirring at room temperature under argon for 2 hours, the reaction mixture was concentrated to dryness in vacuo. The residue was dissolved in $CH_2Cl_2$ (20 mL) and added dropwise over 10 minutes to a solution of olefin 2a (833 mg, 3.24 mmol) and triethylamine (2 mL) in acetone cooled to 0° C. The mixture was stirred overnight under argon and the solvent was removed in vacuo. Purification by column chromatography through silica (1.5% MeOH—$CHCl_3$) afforded 400 mg (45% yield) of the product as a pale pink solid: $^1H$ NMR ($CDCl_3$) $\delta$ 7.66 (s, 2H), 7.22 (m, 8H), 6.23 (m, 4H), 3.48 (m, 4H), 3.41 (m, 4H), 2.81 (m, 4H), 2.08 (m 2H), 1.99 (s, 6H), 1.76, (m, 2H), 1.58 (d, J=8.7 Hz, 2H); $^{13}C$ NMR ($CDCl_3$) 5176.64, 159.90, 150.31, 144.43, 137.01, 135.89, 134.95, 134.68, 129.35, 128.30, 127.67, 122.27, 52.30, 45.83, 45.58, 38.75, 22.88, 15.07; ESMS(+ive): 845.2 ($M+Na^+$, 100%); IR (KBr-cast): 2949 (w), 1709 (s).

Step 2—Polymerization of Bis-bicyclic Olefin 11 to Yield Homopolymer 12

The procedure is identical to that for the polymerization of olefin 5. Thus 11 (81 mg, 0.098 mmol) was polymerized using Grubbs' catalyst (8.1 mg, 0.1 equivalents, 0.05 equivalents per olefin) to yield polymer 12 in 50% yield: $^1H$ NMR ($CDCl_3$) $\delta$ 7.6 (m), 7.3 (m), 6.2 (m), 6.1 (br s), 5.8 (br m), 3.4 (br m), 3.0 (br m), 2.8 (br m), 2.0 (br m). No GPC could be collected as the polymer shows limited solubility in appropriate solvents. Polymer 12 exhibited a color change from colorless to purple upon irradiation with 310-nm light.

Example 4

Preparation of Phenyl Homopolymer 17 (FIG. 5)

Step 1—Synthesis of Phenyl Derivative 14

A mixture of toluene (10 mL) and aqueous $Na_2CO_3$ (2 M, 5 mL) was degassed using argon for 30 minutes after which the mono-iodophotochrome 13 (583 mg, 1.39 mmol) and Pd(Ph$_3$)$_4$ (5 mg) was added. Phenyl boronic acid (186 mg, 1.53 mmol) in dry ethanol (2 mL) was added and the mixture was heated at reflux for 24 hours. The reaction mixture was cooled to room temperature, extracted with ether (3×20 mL) and dried over $Na_2SO_4$. Purification via column chromatography through silica (hexane—1:1 hexane-chloroform gradient) afforded 471 mg (92%) pure product as a pale pink solid: $^1$H NMR (CDCl$_3$) δ 7.47 (m, 2H,), 7.32 (m, 2H), 7.21 (m, 1H), 6.97 (s, 1H), 6.61 (s, 1H), 2.75 (m, 4H), 2.05 (m, 5H), 1.87 (s, 3H); EIMS: 370.1 (M, 100%).

Step 2—Synthesis of Phenyl Carboxylic Acid 15

A solution of chloro-phenylphotochrome 14 (450 mg, 1.2 mmol) in dry THF (20 mL) at −78° C. under argon was treated with tert-butyllithium (0.7 mL of 1.7 M solution in hexane, 1.2 mmol). After stirring for 15 minutes, excess dry CO$_2$ was bubbled through the solution. The reaction mixture was warmed to room temperature, quenched with dilute HCl, extracted with CH$_2$Cl$_2$ (3×50 mL), dried over Na$_2$SO$_4$ and evaporated in vacuo. Purification by column chromatography through silica (3% CH$_3$OH—CH$_2$Cl$_2$) afforded 365 mg (80%) of the product as a pale pink solid: $^1$H NMR (CDCl$_3$) δ 7.64 (s, 1H), 7.48 (m, 2H), 7.29 (m, 2H), 7.21 (m, 1H), 6.95 (s, 1H), 2.80 (m, 4H), 2.04 (m, 2H), 1.97 (s, 3H), 1.94 (s, 3H); $^{13}$C NMR (CDCl$_3$) δ 167.27, 144.93, 140.19, 137.50, 136.24, 136.20, 136.11, 134.48, 134.37, 133.43, 128.85, 128.16, 127.14, 125.39, 123.72, 38.63, 38.61, 27.04, 22.96, 15.02, 14.46; EIMS: 380.1 (M, 100%); IR (KBr-cast): 2952 (broad, m), 1669 (s).

Step 3—Synthesis of Phenyl-monomer 16

A vigorously stirred solution of carboxylic acid 15 (301 mg, 0.79 mmol) and 6 drops of DMF in CH$_2$Cl$_2$ (10 mL) at 0° C. was treated with a solution of oxalyl chloride (502 mg, 3.95 mmol) in CH$_2$Cl$_2$ (5 mL) dropwise over 10 minutes. After stirring at room temperature under argon for 2 hours, the reaction mixture was concentrated to dryness in vacuo. The residue was dissolved in CH$_2$Cl$_2$ (10 mL) and added dropwise over 10 minutes to a solution of olefin 2 (305 mg, 1.19 mmol) and triethylamine (0.5 mL) in acetone cooled to 0° C. The mixture was stirred overnight under argon and the solvent was removed in vacuo. Purification by column chromatography through silica (2% CH$_3$OH—CHCl$_3$) afforded 472 mg (96%) of the product as a pale pink solid: $^1$H NMR (CDCl$_3$) δ 7.73 (s, 1H), 7.47 (m, 2H), 7.31 (m, 2H), 7.22 (m, 1H), 6,97 (s, 1H), 6.55 (m, 2H), 5.38 (m, 2H), 2.98 (m, 2H), 2.84 (m, 4H), 2.10 (m, 2H), 1.99 (s, 3H), 1.98 (s, 3H).

Step 4—Polymerization of Phenyl-bicyclic Olefin 16 to Yield Polymer 17

The procedure is identical to that of monomer 5. Thus 16 (110 mg, 0.18 mmol) was polymerized with Grubbs' catalyst (5.85 mg, 0.04 equivalents) affording polymer 17 in 68% yield. $^1$H NMR (CDCl$_3$) δ 7.7 (br s), 7.4 (br s), 7.2 (br s), 6.95 (br s), 6.1 (br s), 5.8 (br d), 5.2 (br d), 4.6 (br d), 3.4 (br s), 2.8 (br s), 1.9 (m). GPC: Mn=11846, Mw=17536, Polydispersity Index=1.48. Polymer 17 exhibited a color change from colorless to purple upon irradiation with 254-nm light.

The polymers described in this application lend support to the mildness of the ROMP process. The selective ring-opening of the strained olefin in the monomer should be emphasized. As will be apparent from the above examples, the ROMP process produces homopolymers rather than copolymers. This provides macroscopic materials that have an increased density of photochromic units, a feature that is very advantageous for practical applications. Another advantage of using the ROMP technology is that by varying the catalyst-to-substrate stoichiometry, ROMP allows the polymer chain length to be readily tailored. For example, extremely dense glass-like polymers having a very large number of photochromic units (n≧100) could be prepared.

While the present invention has been described with reference to what are presently considered to be preferred examples, it is to be understood that the invention is not limited to the disclosed examples. On the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification 1. (a) Irie, M. In *Organic Photochromic and Thermochromic Compounds*; Crano, J. C., Gugliemetti, R. J., Eds.; Plenum Press: New York, N.Y., 1999; volume 1, chapter 5, pages 207–222. (b) Irie, M.; Mohri, M. *J. Org. Chem.* 1988, 53, 803. (c) Gilat, S. L.; Kawai, S. H.; Lehn, J.-M. *Chem Eur. J.* 1995, 1, 275.
2. Wakashima, H.; Irie, M. *Polymer Journal* 1998, 30, 985 and references therein.
3. Ichimura, K. In *Organic Photochromic and Thermochromic Compounds*; Crano, J. C., Gugliemetti, R. J., Eds.; Plenum Press: New York, N.Y., 1999; volume 2, chapter 1, pages 9–63.
4. For other examples of photochromic polymers see: (a) Kumar, G. S.; Neckers, D. C. *Chem. Rev.* 1989, 89, 1915. (b) Warshawsky, A.; Kahana, N.; Buchholtz, F.; Zelichonok, A.; Ratner, J.; Krongauz, V. *Ind. Eng. Chem. Res.* 1995, 34, 2825. (c) Buchholtz, F.; Zelichenok, A.; Krongauz, V. *Macromolecules* 1993, 26, 906. (d) Lyubimov, A. V.; Zaichenko, N. C.; Marevtsev, V. S. *J. Photochem. Photobiol. A: Chem.* 1999, 120, 55.
5. Grubbs, R. H.; Tumas, W. *Science* 1989, 243, 907. (b) Wu, Z.; Benedicto, A. D.; Grubbs, R. H. *Macromolecules* 1993, 26, 4975. (c) Robson, D. A.; Gibson, V. C.; Davies, R. G.; North, M. *Macromolecules* 1999, 32, 6371 and references cited therein.
6. For other examples of polymers using dithienyl and diarylalkenes see: a) Wakashima, H.; Irie, M. *Polymer Journal* 1998, 30, 985–989. b) Kawai, T.; Kunitake, T.; Irie, M. *Chem. Lett.* 1999, 905–906. c) Stellacci, F.; Bertarelli, C.; Toscano, F.; Gallazzi, M. C.; Zotti, G.; Zerbi, G. *Advanced Materials*, 1999, 64, 292–295. d) Munakata, M.; Wu, L. P.; Kuroda-Sowa, T.; Maekawa, M.; Suenaga, Y.; Furuichi, K. *J. Am. Chem. Soc.* 1996, 118, 3305–3306.
7. For recent examples of the use of this catalyst see ref. 5 and Montalban, A. G.; Steinke, J. H. G.; Anderson, M. E.; Barrett, A. G. M.; Hoffman, B. M. *Tet. Lett.* 1999, 40, 8151–8155.
8. Bolm, C; Dinter, C. L.; Seger, A.; Höcker, H.; Brozio, J. *J. Org. Chem.* 1999, 64, 5730.
9. Salakhov *J. Org. Chem. USSR English Translation* 1979, 2106–2112.
10. Lucas, L. N.; van Esch, J.; Kellog, R. M.; Feringa, B. L. *Chem. Commun.* 1998, 2313.
11. Lucas, L. N.; van Esch, J.; Kellogg, R. M.; Feringa, B. L. *Tetrahedron Lett.* 1999, 1775–1778.
12. Norsten, T. B.; Branda, N. R. *J. Am. Chem. Soc.* 2001, 1784–1785.

TABLE 1

POLYMER YIELDS AND CHARACTERIZATION

| Photochrome | Equivalents monomer | Yield | $M_n$ | $M_w$ | $M_w/M_n$ | $\lambda_{max}$ (nm) open form | $\lambda_{max}$ (nm) closed form |
|---|---|---|---|---|---|---|---|
| 1a | 25 | 76 | 7920 | 11917 | 1.50 | 248 | 512 |
| 1b | 50 | 78 | 16771 | 24577 | 1.47 | 248 | 512 |
| 1c | 100 | 75 | 28007 | 43820 | 1.56 | 248 | 512 |
| 5  | — | — | — | — | — | 248 | 512 |
| 9  | 25 | 53 | 7437 | 10953 | 1.47 | 250 | 559 |
| 8  | — | — | — | — | — | 250 | 559 |
| 12 | 10 | 50 | — | — | — | 266 | 562 |
| 11 | — | — | — | — | — | 266 | 562 |
| 17 | 25 | 68 | 11846 | 17536 | 1.48 | 270 | 553 |
| 16 | — | — | — | — | — | 270 | 553 |

What is claimed is:

1. A homopolymer of the Formula I:

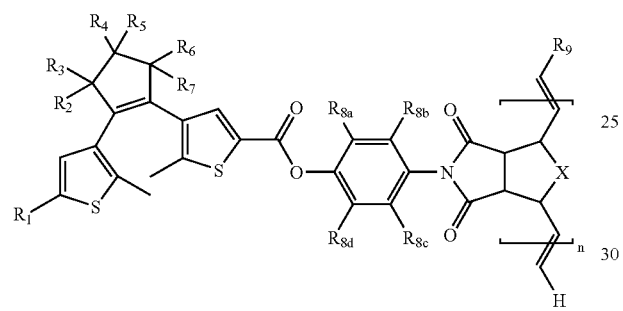

wherein:

n is any positive integer;

X is $CH_2$, $CHR_{10}$, O, S, NH, N-alkyl, N-aryl, or $CH_2$—$CH_2$;

$R_1$ is selected from the group consisting of H, a halogen, a carboxylic acid, an ester, an aldehyde, an alkene, a phenyl, an aryl and structure A, where structure A is:

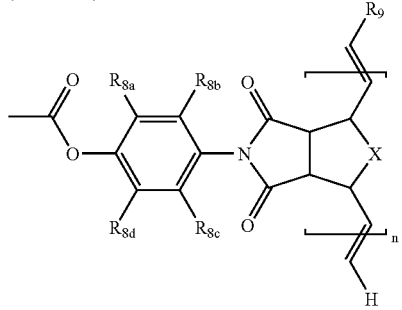

$R_2$, $R_3$, $R_4$, $R_5$, $R_6$ and $R_7$ are each selected from the group consisting of H and a halogen;

$R_{8a}$, $R_{8b}$, $R_{8c}$ and $R_{8d}$ are each selected from the group consisting of H, an alkyl and a halogen;

$R_9$ is a phenyl or an aryl; and, $R_{10}$ is an alkyl, an aryl or a phenyl.

2. A homopolymer according to claim 1, wherein $R_1$ is chlorine, phenyl or structure A.

3. A homopolymer according to claim 1, wherein $R_2$, $R_3$, $R_4$, $R_5$, $R_6$ and $R_7$ are H or fluorine.

4. A homopolymer according to claim 1, wherein X is $CH_2$ or O.

5. A homopolymer according to claim 1, wherein $R_1$ is structure A and the homopolymer is cross-linked.

6. A homopolymer according to claim 1, wherein n is from 10 to 100.

7. A homopolymer according to claim 1, wherein n is 25.

8. A homopolymer according to claim 1, wherein n is 50.

9. A homopolymer according to claim 1, wherein n is 100.

10. A method of preparing a homopolymer according to claim 1 comprising carrying out the reaction steps set forth in any one of the following synthetic schemes A, B, C and D;

Scheme A

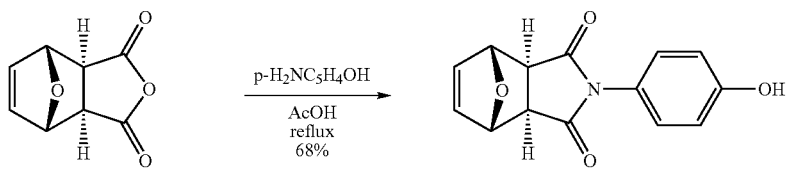

-continued
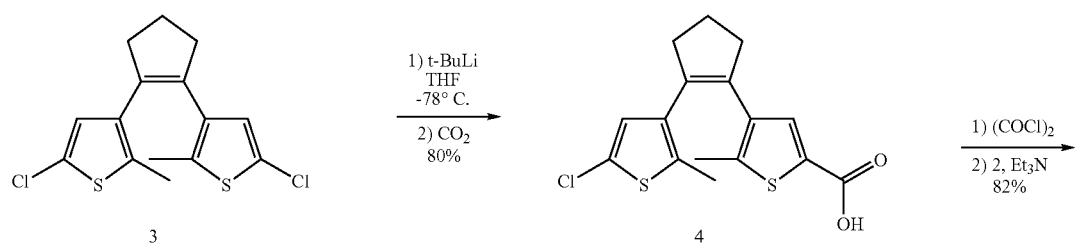
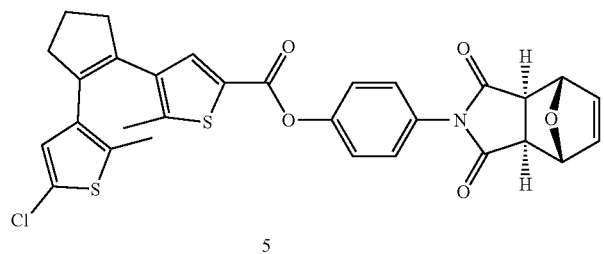
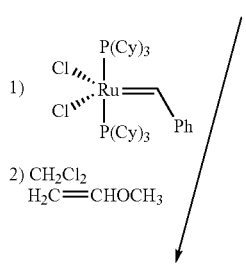
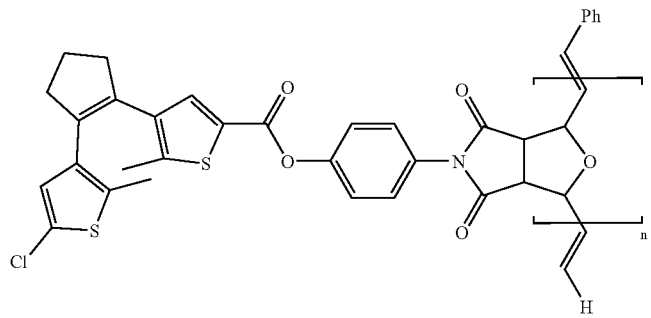
1a  n = 25
1b  n = 50
1c  n = 100
Scheme B
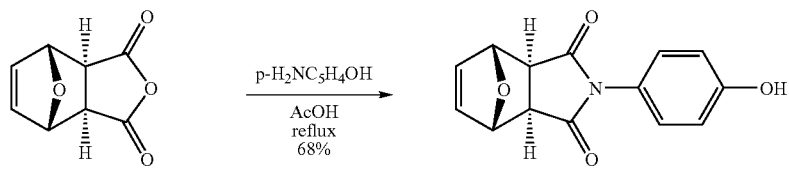

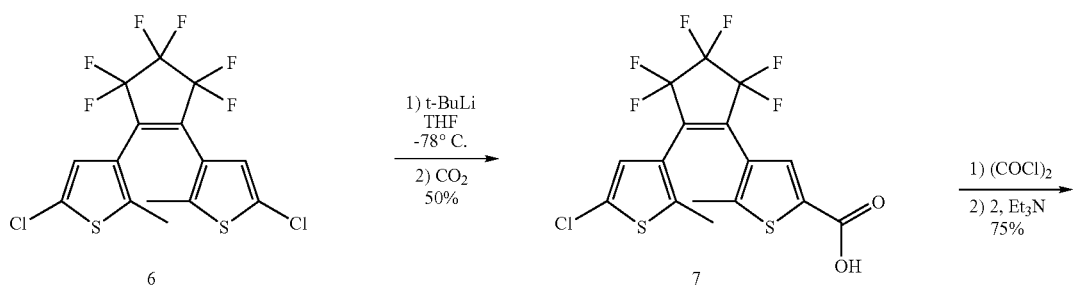
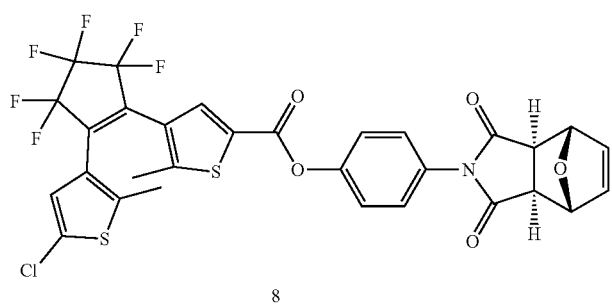
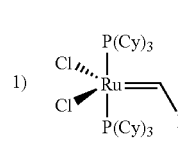
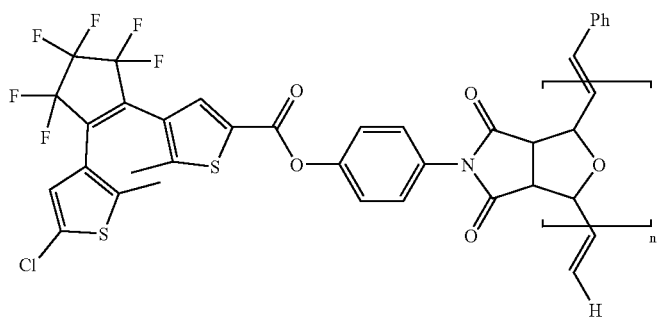
9 n = 25
Scheme C
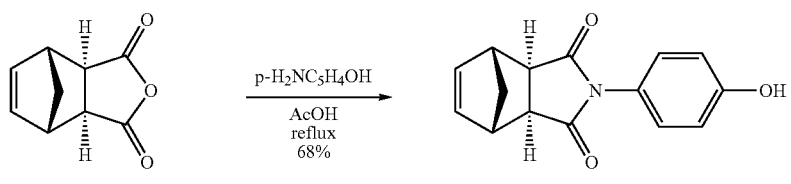

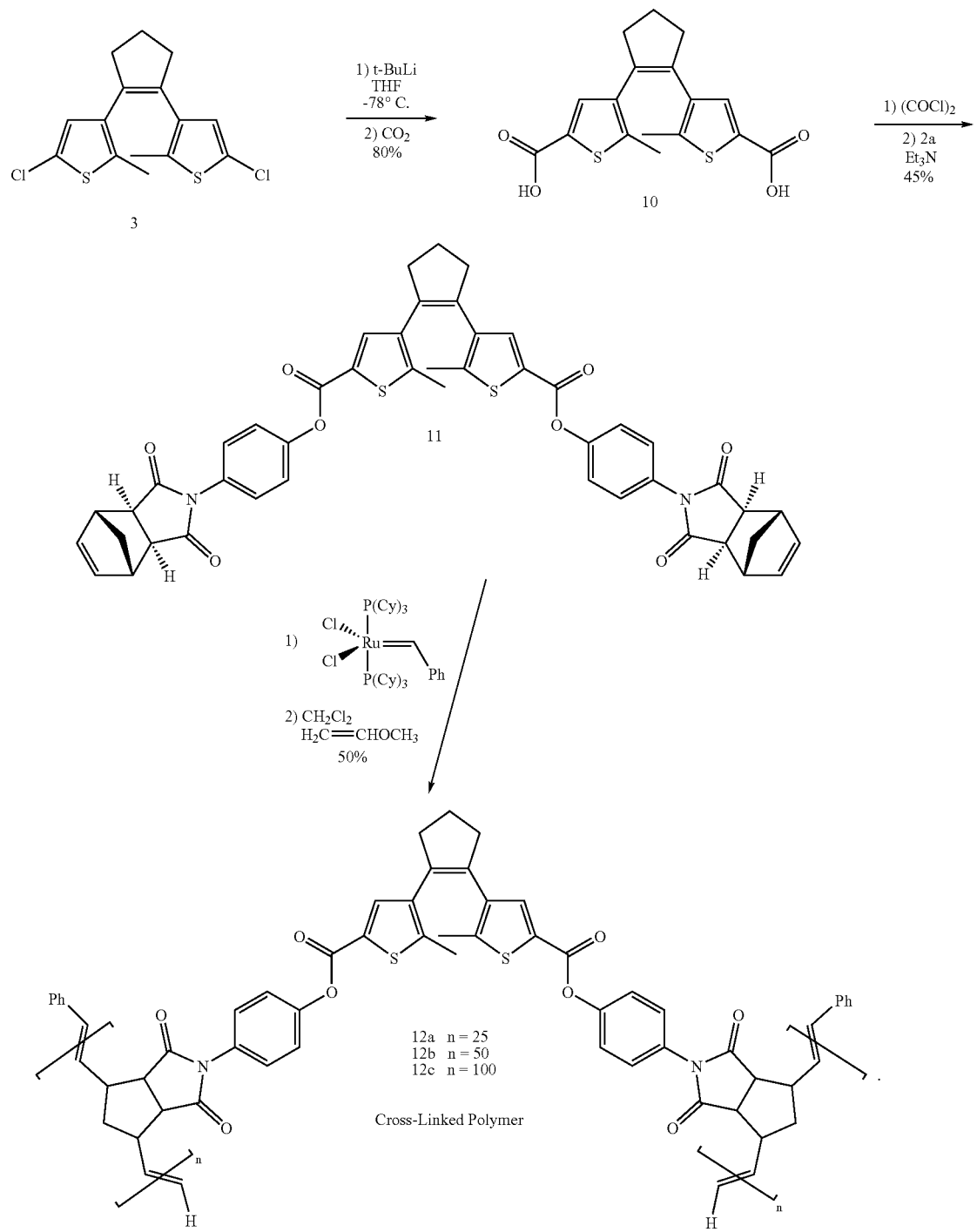
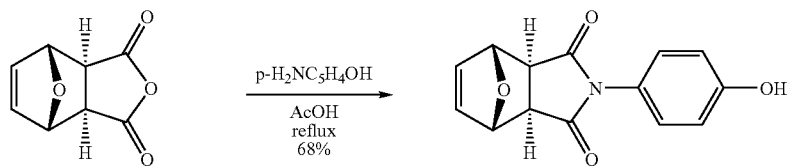
Scheme D

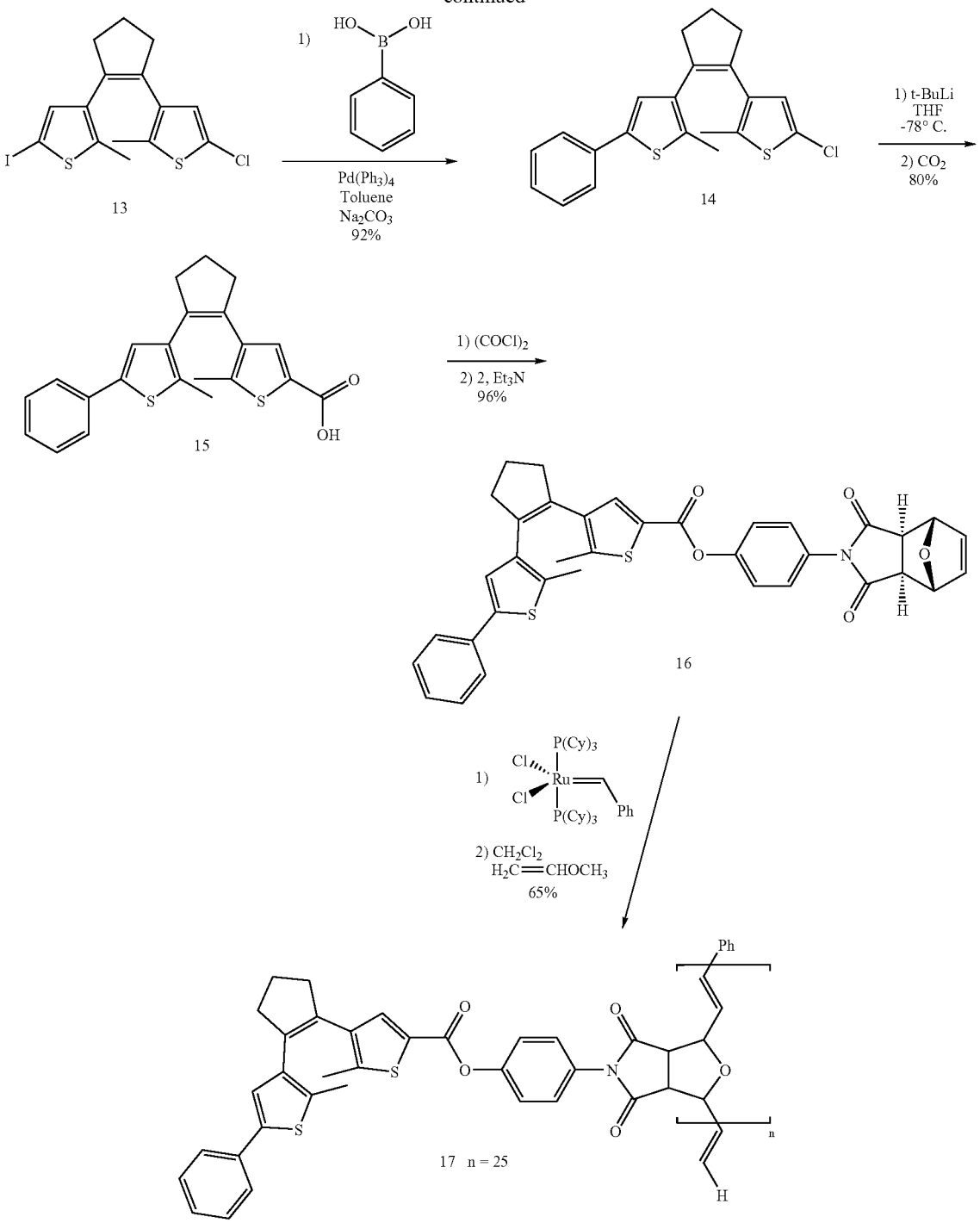

-continued

11. A method of preparing a photochromic homopolymer using ring-opening metathesis polymerization of a photochromic monomer containing a photochromic dithienylethene pendant group.

12. A method of fabricating a manufacture comprising incorporating in said manufacture a homopolymer according to claim 1.

13. The method as defined in claim 12, wherein said manufacture is selected from the group consisting of:
   (1) opthalmic lenses-eyeglasses that change color depending on the ambient light;
   (2) actinometric devices and molecular sensors;
   (3) novelty items such as photochromic inks, paints and fibers;
   (4) variable transmission filters—those that on command, regulate the amount and type of light that can be transmitted;
   (5) high-density optical information storage systems (this invention is particularly well-suited to this application as it provides more information storage sites per unit area), (6) photo-regulated molecular switches that can be incorporated into molecular-scale machinery;
(7) optoelectronic systems; and
(8) reversible holographic systems.

14. A polymer comprising a compound of Formula VI:

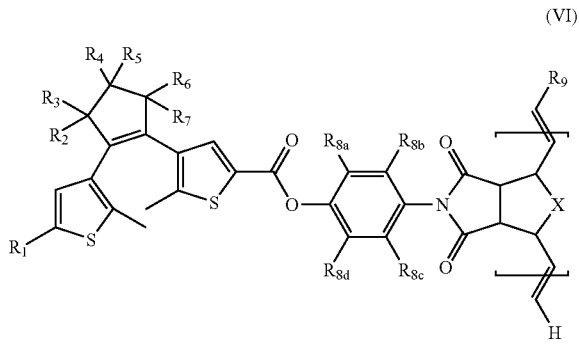

(VI)

wherein:
X is $CH_2$, $CHR_{10}$, O, S, NH, N-alkyl, N-aryl, or $CH_2$—$CH_2$;
$R_1$ is selected from the group consisting of H, a halogen, a carboxylic acid, an ester, an aldehyde, an alkene, a phenyl, an aryl and structure A, where structure A is:

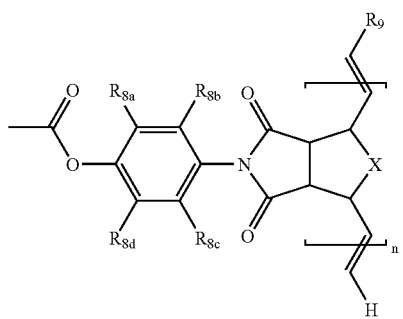

$R_2$, $R_3$, $R_4$, $R_5$, $R_6$ and $R_7$ are each selected from the group consisting of H and a halogen;
$R_{8a}$, $R_{8b}$, $R_{8c}$, and $R_{8d}$ are each selected from the group consisting of H, an alkyl and a halogen;
$R_9$ is a phenyl or an aryl; and,
$R_{10}$ is an alkyl, an aryl or a phenyl.

15. A method for polymerization of photochromic dithienyl-alkene monomers to yield photochromic homopolymers comprising performing said polymerization in the presence of Grubbs' catalyst.

16. The method of claim 15, wherein said photochromic monomer is 1,2-bis-(3-thienyl)-cyclopentene.

17. A method of fabricating a manufacture comprising incorporating in said manufacture a homopolymer according to claim 2.

18. The method as defined in claim 17, wherein said manufacture is selected from the group consisting of:
(1) opthalmic lenses-eyeglasses that change color depending on the ambient light;
(2) actinometric devices and molecular sensors;
(3) novelty items such as photochromic inks, paints and fibers;
(4) variable transmission filters—those that on command, regulate the amount and type of light that can be transmitted;
(5) high-density optical information storage systems (this invention is particularly well-suited to this application as it provides more information storage sites per unit area),
(6) photo-regulated molecular switches that can be incorporated into molecular-scale machinery;
(7) optoelectronic systems; and
(8) reversible holographic systems.

19. A method of fabricating a manufacture comprising incorporating in said manufacture a homopolymer according to claim 3.

20. The method as defined in claim 19, wherein said manufacture is selected from the group consisting of:
(1) opthalmic lenses-eyeglasses that change color depending on the ambient light;
(2) actinometric devices and molecular sensors;
(3) novelty items such as photochromic inks, paints and fibers;
(4) variable transmission filters—those that on command, regulate the amount and type of light that can be transmitted;
(5) high-density optical information storage systems (this invention is particularly well-suited to this application as it provides more information storage sites per unit area),
(6) photo-regulated molecular switches that can be incorporated into molecular-scale machinery;
(7) optoelectronic systems; and
(8) reversible holographic systems.

21. A method of fabricating a manufacture comprising incorporating in said manufacture a homopolymer according to claim 4.

22. The method as defined in claim 21, wherein said manufacture is selected from the group consisting of:
(1) opthalmic lenses-eyeglasses that change color depending on the ambient light;
(2) actinometric devices and molecular sensors;
(3) novelty items such as photochromic inks, paints and fibers;
(4) variable transmission filters—those that on command, regulate the amount and type of light that can be transmitted;
(5) high-density optical information storage systems (this invention is particularly well-suited to this application as it provides more information storage sites per unit area),
(6) photo-regulated molecular switches that can be incorporated into molecular-scale machinery;
(7) optoelectronic systems; and
(8) reversible holographic systems.

23. A method of fabricating a manufacture comprising incorporating in said manufacture a homopolymer according to claim 5.

24. The method as defined in claim 23, wherein said manufacture is selected from the group consisting of:
(1) opthalmic lenses-eyeglasses that change color depending on the ambient light;
(2) actinometric devices and molecular sensors;
(3) novelty items such as photochromic inks, paints and fibers;
(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

25. A method of fabricating a manufacture comprising incorporating in said manufacture a homopolymer according to claim 6.

26. The method as defined in claim 25, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

27. A method of fabricating a manufacture comprising incorporating in said manufacture a homopolymer according to claim 7.

28. The method as defined in claim 27, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

29. A method of fabricating a manufacture comprising incorporating in said manufacture a homopolymer according to claim 8.

30. The method as defined in claim 29, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

31. A method of fabricating a manufacture comprising incorporating in said manufacture a homopolymer according to claim 9.

32. The method as defined in claim 31, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

33. A homopolymer according to claim 2, wherein n is from 10 to 100.

34. A method of fabricating a manufacture comprising incorporating in said manufacture a homopolymer according to claim 33.

35. The method as defined in claim 34, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

36. A homopolymer according to claim 2, wherein n is 25.

37. A method of fabricating a manufacture comprising incorporating in said manufacture a homopolymer according to claim 36.

38. The method as defined in claim 37, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—these that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

39. A homopolymer according to claim 1, wherein n is 50.

40. A method of fabricating a manufacture comprising incorporating in said manufacture a homopolymer according to claim 39.

41. The method as defined in claim 40, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

42. A homopolymer according to claim 1, wherein n is 100.

43. A method of fabricating a manufacture comprising incorporating in said manufacture a homopolymer according to claim 42.

44. The method as defined in claim 43, wherein said manufacture is selected from the group consisting of:

(1) opthalmic lenses-eyeglasses that change color depending on the ambient light;

(2) actinometric devices and molecular sensors;

(3) novelty items such as photochromic inks, paints and fibers;

(4) variable transmission filters—those that on command, regulate the amount and type of light that can be transmitted;

(5) high-density optical information storage systems (this invention is particularly well-suited to this application as it provides more information storage sites per unit area), (6) photo-regulated molecular switches that can be incorporated into molecular-scale machinery;

(7) optoelectronic systems; and (8) reversible holographic systems.

\* \* \* \* \*